United States Patent [19]
Herczeg

[11] Patent Number: 5,490,927
[45] Date of Patent: Feb. 13, 1996

[54] FILTRATION APPARATUS WITH MEMBRANE FILTER UNIT

[75] Inventor: Attila E. Herczeg, Concord, Mass.

[73] Assignee: Filtron Technology Corporation, Northborough, Mass.

[21] Appl. No.: 368,473

[22] Filed: Jan. 4, 1995

[51] Int. Cl.$^6$ .................................. B01D 63/00
[52] U.S. Cl. .................. 210/321.84; 210/321.75; 210/450; 210/451; 210/445; 210/433.1; 210/455; 422/101; 422/102; 422/103
[58] Field of Search ............... 210/321.84, 321.75, 210/321.6, 477, 479, 450, 451, 45, 256, 416.1, 445, 433.1; 422/101–103

[56] References Cited

U.S. PATENT DOCUMENTS

| | | | |
|---|---|---|---|
| 3,488,768 | 1/1970 | Rigopulos . | |
| 4,614,585 | 9/1986 | Mehra et al. | 210/321.84 |
| 4,632,761 | 12/1986 | Bowers | 210/650 |
| 4,783,318 | 11/1988 | Lapakko | 210/416.1 |
| 4,849,061 | 7/1989 | Relyea | 210/455 |
| 5,112,484 | 5/1992 | Zuk, Jr. | 210/247 |
| 5,234,585 | 8/1993 | Zuk, Jr. | 210/416.1 |
| 5,308,483 | 5/1994 | Sklar et al. | 210/321.75 |

Primary Examiner—Ana M. Fortuna
Attorney, Agent, or Firm—Heslin & Rothenberg

[57] ABSTRACT

A filtration apparatus for separating filtrate and concentrate from a liquid solution is disclosed. The filtration apparatus contains a housing having a discharge opening therein and being capable of containing a liquid solution to be filtered therein. A filter unit is insertable within the housing such that a first side faces the discharge opening of the housing. The filter unit contains a semipermeable membrane located thereon and capable of separating filtrate and concentrate. At least one inlet is located within the first side so that the semipermeable membrane covers the inlets.

20 Claims, 6 Drawing Sheets

5,490,927

FILTRATION APPARATUS WITH MEMBRANE FILTER UNIT

BACKGROUND OF THE INVENTION

This invention relates to the filtration field, and more particularly, to an improved filtration apparatus for filtering and concentrating a solution.

It is well known that the filtration of fluids may be accomplished through the use of filtration devices which utilize sub-micron filters to filter and concentrate a macromolecular solution. This technique has been utilized in centrifugal filtration apparatuses which rely on centrifugal forces to direct solutions towards a filter which separates liquid solutions into filtrate and concentrate.

There are certain drawbacks, however, associated with the conventional centrifugal filtration apparatus. Typically, such an apparatus contains a filter unit covering the bottom portion of a housing so that the centrifugal force draws the liquid solution towards the filter unit. One disadvantage with this type of system is that the filtration surface area is relatively small when compared to the volume of liquid solution within the housing. Therefore, filtration occurs at a relatively slow rate. Secondly, the filtration devices contain a semipermeable membrane filter which is conducive to clogging because the more dense molecules within the liquid solution are forced onto the membrane filter.

Another problem with certain conventional filtration devices is their propensity to filter a solution to dryness so that all of the solution will have been filtered. The apparatus continues to run despite all of the concentrate being filtered. Generally, filtration to dryness should be avoided because the recovery and biological feasibility of concentrate is significantly reduced.

Certain types of filtration devices, such as that disclosed in U.S. Pat. No. 4,632,761 to Bowers et al., are capable of preventing filtration to dryness and contain a "dead stop" feature which causes filtration to cease while there is concentrate remaining within the apparatus. The Bowers et al. device, however, filters to dryness when spun at a 90° angle if the device is spun in a swinging bucket centrifuge. Also, in this type of filtration device, the amount of the concentrate remaining after dead stop is dependent upon the angle of rotation of the apparatus. The amount of concentrate remaining in the apparatus is varied by varying the angle at which the apparatus is rotated. However, which this is impossible to do with fixed angle centrifuge rotors. Accordingly, this device will filter to dryness when spun in a swinging bucket centrifuge and cease filtration at only one concentration level when spun in a fixed angle centrifuge.

U.S. Pat. No. 5,112,484 to Zuk depicts a filtration apparatus having a multiple sided filter unit, for separating filtrate from concentrate, which is mounted therein so that the semipermeable membrane is oriented at a direction substantially perpendicular to the centrifugal force applied to the solution to be filtered when the filtration apparatus is used in a centrifuge. In this device, however, the concentrated material becomes increasingly concentrated during the filtration process resulting in the filtration rate progressively declining during use. Moreover, the pressure created by the head of liquid to be filtered decreases as the liquid is filtered through the membrane therefore progressively reducing the filtration rate. During operation of this device, the amount of membrane exposed to the liquid to be filtered diminishes as the fluid is filtered through the membrane thereby also reducing the filtration rate of the device. The pressure head on the membrane is not constant at any given filtration time and the pressure exerted along the membrane varies with the vertical position of the membrane surface.

It is therefore desirable to provide a filtration device which improves filtration rate during operation, minimizes the effects of a diminishing pressure head which results as filtration time increases, operates without variation of the membrane surface area exposed to liquid being filtered and/or filters at a uniform head pressure on the membrane surface.

It is also desirable to provide a filtration device which may be used without filtering to dryness, which has a relatively high filtration membrane surface area thereby enabling filtration to occur at a relatively higher rate, minimizes the clogging of the semi-permeable membrane thereby maximizing filter efficiently, and/or is self-cleaning and, therefore, reusable.

It is also desirable to provide a filtration device which allows dense molecules which may cause fouling to be forced away from the membrane surface by centrifugal force while simultaneously allowing filtrate to flow into a filtrate collection means.

SUMMARY OF INVENTION

The aforementioned advantages may be achieved by using a filtration apparatus for separating filtrate and concentrate from a solution in accordance with the principles of the present invention. The filtration apparatus includes a housing having a discharge opening therein and being capable of containing a solution therein, a filter unit insertable within the housing wherein a first side thereof faces the discharge opening of the housing. The filter unit may include a semipermeable membrane located on the first side capable of separating filtrate and concentrate, at least one inlet located within the first side wherein said semipermeable membrane covers at least one inlet, a filtrate port located within the first side and being in fluid flow relationship with at least one inlet, wherein said filtrate port is oriented to allow filtrate flowing therethrough to flow into the discharge opening of the filtration apparatus, and means for sealing the filter unit to the housing for preventing concentrate within the housing from flowing within the discharge opening.

The filter unit may include a neck protruding from the first side thereof, the neck having the filtrate port therein and being insertable into the discharge opening of the housing. The sealing means may include an interface between the neck and the discharge opening. The housing may include a removable cap.

The filtration apparatus may further include a means for collecting the concentrate. The means for collecting the concentrate may include a concentrate collecting cup having a protruding member therein insertable within the discharge opening of the housing. When the protruding member is inserted into the discharge opening, the filter unit is displaced to allow concentrate from within the housing to flow through said discharge opening and into the concentrate cup.

The filtration apparatus may also include means for receiving the concentrate cup. The means for receiving the concentrate collecting cup may include a threaded member capable of receiving a threaded portion of the concentrate collecting cup.

Also, the filtration apparatus may include a means for collecting filtrate. The means for collecting filtrate may include a filtrate collecting cup. Also, the filtration apparatus may include means for securing the filtrate collecting cup to the housing.

A plurality of filter inlets may be located around the periphery of a portion of the first side of the filter unit having the neck protruding therefrom. The semipermeable membrane may be sealed to the first side of the filter unit. The first side of the filter unit may include at least one groove thereon for allowing filtrate to flow therein to the filtrate port.

BRIEF DESCRIPTION OF THE DRAWINGS

These and other objects, features and advantages of the invention will be evident from the following detailed description when read in conjunction with the accompanying drawings in which.

DETAILED DESCRIPTION OF PREFERRED EMBODIMENT

Figure 1:
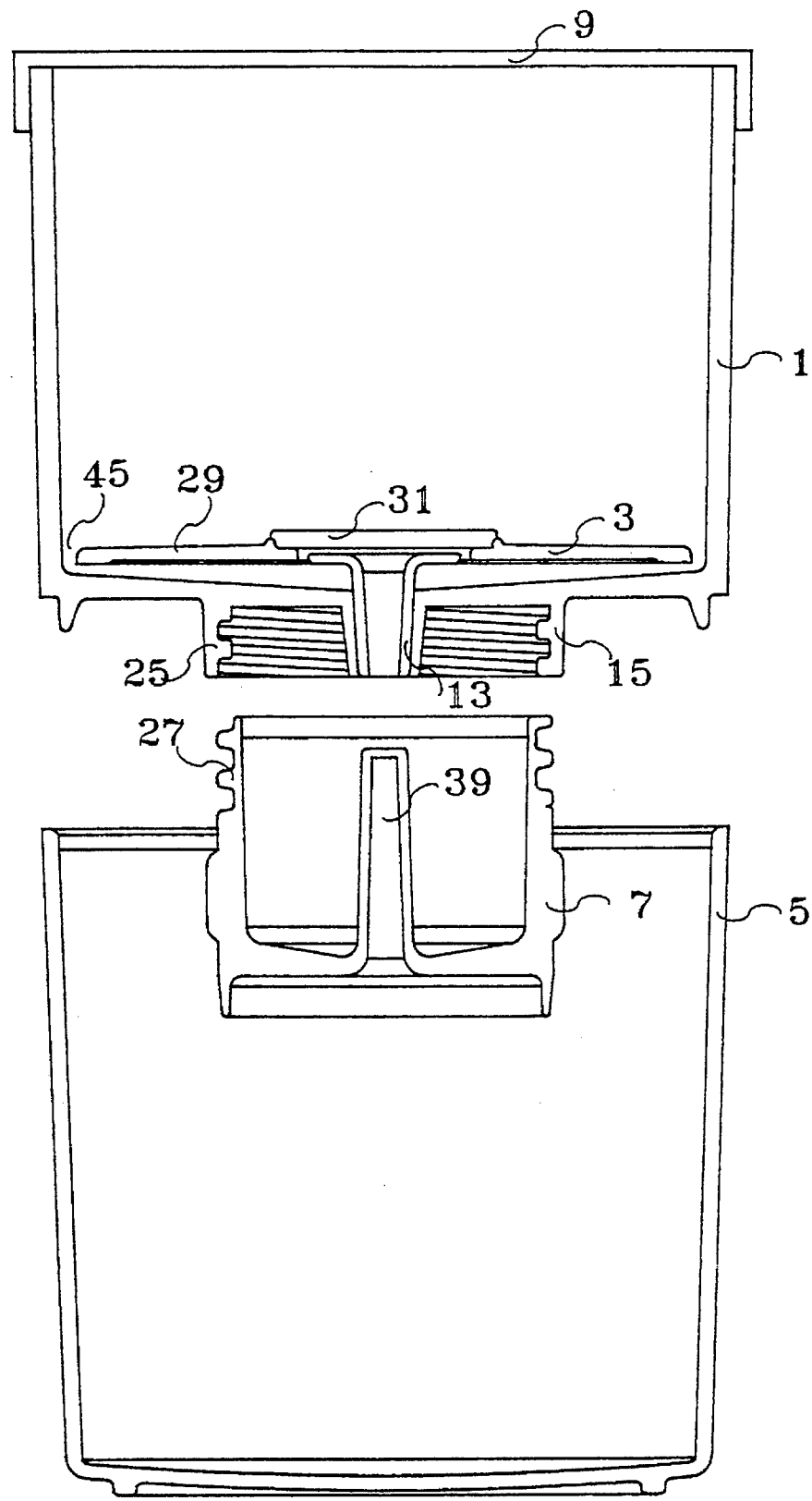
FIG. 1 depicts a sectional view of a filtration apparatus constructed in accordance with the principles of the present invention.

The improved filtration apparatus of the present invention may be embodied in a batch process filtration device such as that shown in FIG. 1, useable in a centrifuge. The filtration device includes a housing 1, a filter unit 3, a filtrate cup 5, a concentrate cup 7, and a cap 9. The structure and function of the components will now be described in detail.

Referring to FIG. 1, a preferably cup shaped housing 1 is capable of holding a liquid solution to be filtered therein. The housing 1 contains a removable cap 9. At the lower portion of the housing 1, a discharge opening 11 (FIG. 5) is located. The discharge opening 11 may extend through a nipple 13 protruding from the lower portion of the housing 1. Preferably, the nipple is conical in shape having a diameter decreasing at increasing distances from the lower portion of the housing 1. The removable cap 9 may be constructed to allow air to pass therethrough into the housing 1. Preferably, the housing 1 is vented by using a vented removable cap 9.

The filtration apparatus may also include a filtrate collecting means including a filtrate collector such as a filtrate collecting cup 5. However, other suitable filtrate collectors may suffice. The filtrate collecting cup 5 may be connected to the housing by a press-fit wherein the filtrate collecting cup and housing are sized and configured accordingly. Also, other means for connecting the filtrate collecting cup 5 to the housing 1 may be used. For example, the filtrate collecting cup 5 may be threadably engagable to the housing 1, snap-fit to the housing or fastened thereto by a fastener or the like. In order to prevent pressure build-up within the filtrate collecting cup 5, the cup should be vented. Venting may be facilitated by preventing an air-tight seal between the filtrate collecting cup 5 and the housing 1. Alternatively, the side of the filtrate cup may contain one or more direct vents (not shown) to allow air to pass from within the filtrate collecting cup 5.

The filtration apparatus may also include a concentrate collecting means including a concentrate collector such as a concentrate collecting cup 7, described infra, or the like. Although FIG. 1 depicts both a concentrate collecting cup 7 and a filtrate collecting cup 5, the filtrate collecting cup 5 is first attached to the housing without the concentrate collecting cup 7 being attached thereto. After filtration, the concentrate collecting cup 7 will then be attached to the housing 1. As shown in FIG. 1, if a concentrate collecting cup 7 is used as the concentrate collector, a threaded collar 15 may be used as a means for securing the concentrate collecting cup 7 to the housing 1. The threaded collar 15 may protrude from the bottom portion of the housing 1 and contain threads 26 which are threadably engagable to threads 27 located on the concentrate collecting cup 7 to secure the concentrate collecting cup 7 to the housing 1. Other suitable means for securing the concentrate collecting cup to the housing 1 may also be used. For example, the concentrate collecting cup 7 and housing 1 may be configured so that the concentrate collecting cup is secured to the housing 1 by a snap-fit, fastener, or press-fit, etc.

Figure 2:
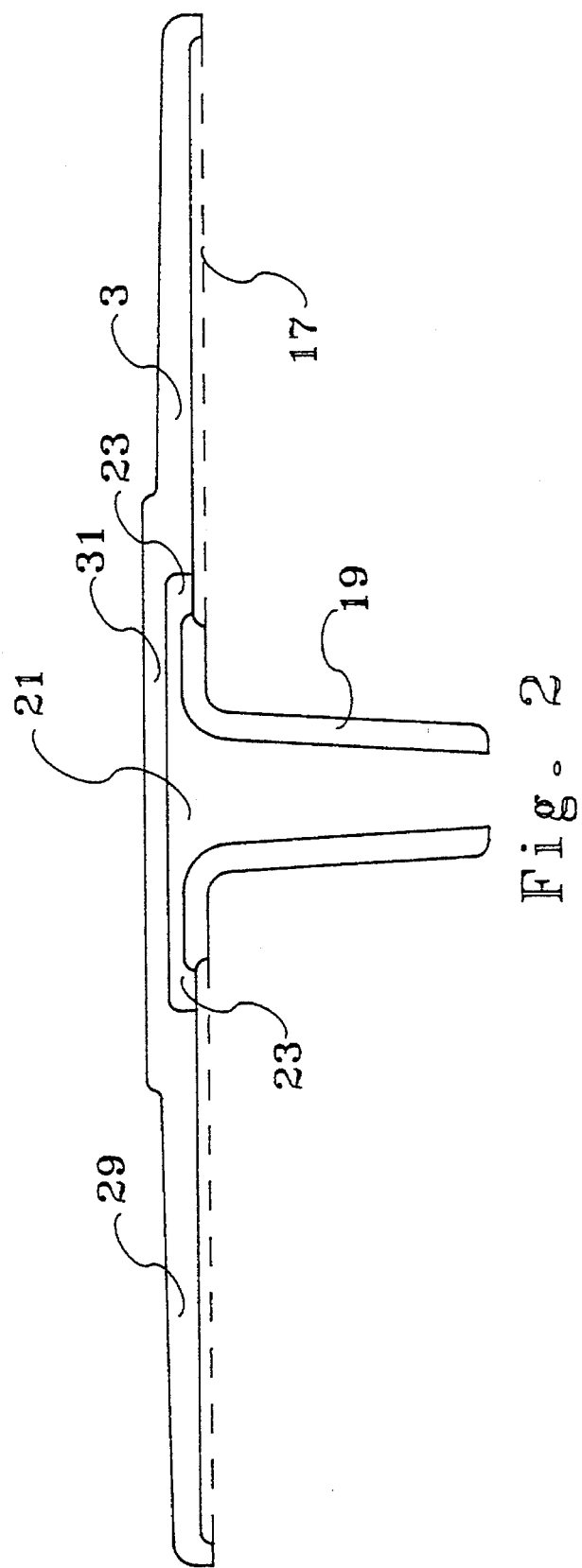
FIG. 2 depicts a sectional view of a filter unit useable within the filtration apparatus of FIG. 1 and also constructed in accordance with the principles of the present invention.

The filtration apparatus also includes a filter unit 3. The filter unit 3 is insertable within the housing 1 to allow filtrate to flow within the filter unit and through the discharge opening 13. As shown in FIG. 1, the filter unit may contain a first section 29 and a second section 31, affixed thereto. Alternatively, as shown in FIG. 2, the filter unit may contain an integrally formed first section 29 and second section 31. Referring to FIG. 2, the filter unit 3 contains a semipermeable membrane 17 capable of separating filtrate and concentrate from a liquid solution such as blood, blood products and/or other macro-molecular products. Semipermeable membrane materials capable of this type of filtration are well known in the art.

Figure 4:
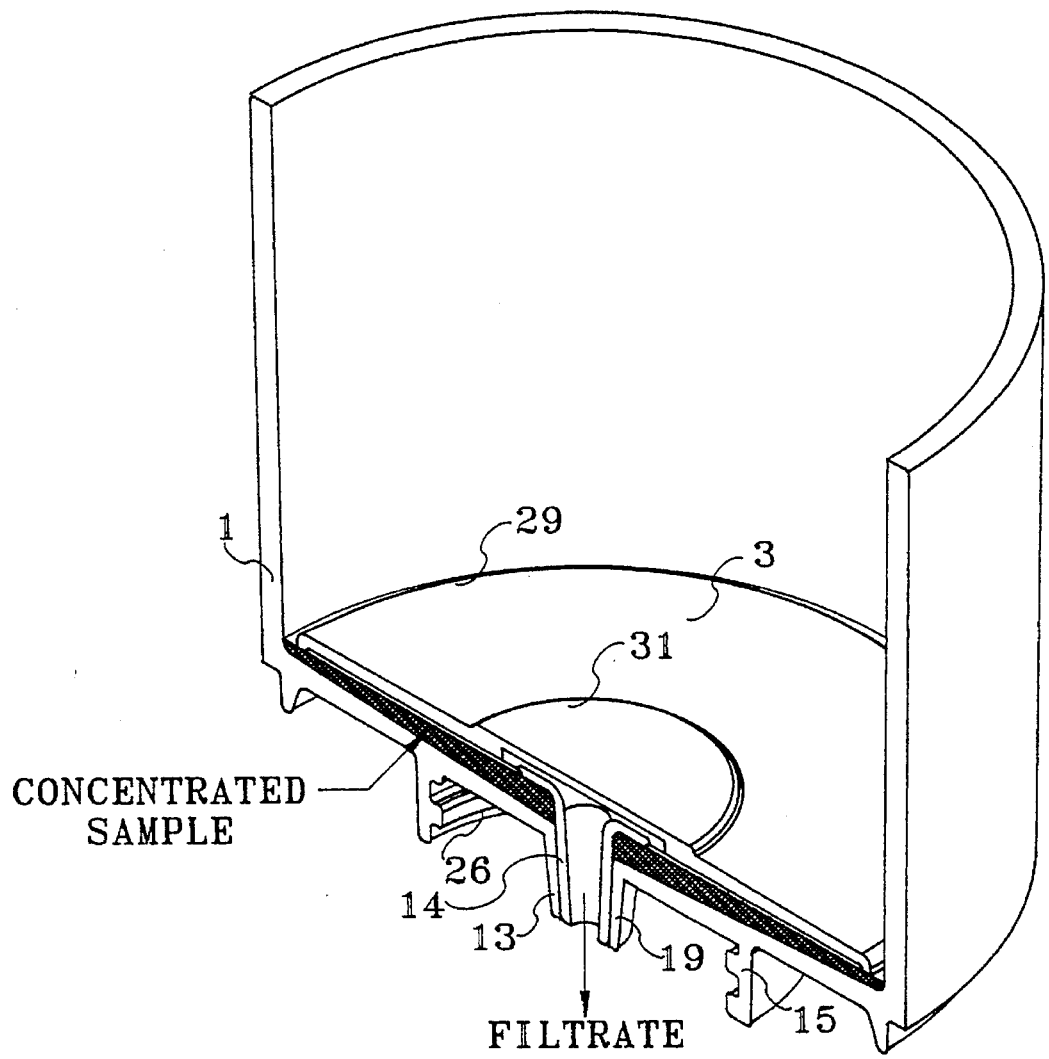
FIG. 4 depicts a sectional isometric view of a housing and filter element useable within the filtration apparatus containing concentrated sample therein in accordance with the principles of the present invention.

The semipermeable membrane 17 is located on a first side of the filter unit 3 and is preferably heat sealed thereto. However, the semipermeable membrane may also be ultrasonically sealed, glued or sealed by any other means to the first side, i.e., underside, of the filter unit. The first side of the filter unit 3 faces the discharge opening 13 of the housing 1 so that the semipermeable membrane 17 affixed thereto faces the discharge opening 13 and the bottom portion of the housing. The semipermeable membrane should be oriented to be facing opposite the direction the force exerts on the liquid thereby preventing the denser molecules from contacting the semipermeable membrane. The denser molecules are driven by centrifugal force to the bottom portion of the housing 1 which minimizes macro-molecular build up on the membrane surface while allowing solvent liquid to readily pass through the membrane. Moreover, to maximize filtration rate the surface area of the semipermeable membrane should be maximized. As shown in FIG. 1 and 4, the semipermeable membrane covers almost the entire surface area of first side of the filter unit which is, preferably, almost identical in size to the diameter of the housing. A relatively small gap 45 is located, however, between the filter unit 3 and the side of the housing 1 to allow the liquid to be filtered to pass therethrough and contact the semipermeable membrane so that the pressure exerted on the liquid within the housing 1 forces the filtrate through the semipermeable membrane. A neck 19 may protrude from the first side of the filter unit 3. A filtrate port 21 located within the first side of the filter unit 3 should be placed in fluid flow relationship with inlets 23 located within the first side of the filter unit 3 and covered by the semipermeable membrane 17. The inlets 23 may form a passage leading to the filtrate port which extends through the neck 19. Liquid filtrate, filtered through the membrane may, therefore, pass into the inlets 23 and flow through the filtrate port 21, through the neck 19 and into the filtrate collecting means, such as the filtrate collecting cup 5 (FIG. 1).

As shown in FIG. 1, the filter unit 3 is insertable into the housing 1 wherein the semipermeable membrane 17 (FIG. 2) faces the lower portion of the housing 1. The filtrate port 21 should thereby be placed in fluid flow relationship with the discharge opening 21 by inserting the neck 19 into the nipple 13. The neck 19 should be sized in relation to the nipple 13 such that the interface 14 therebetween creates a seal to prevent fluid from flowing therebetween. However, other means for sealing the filter unit to the housing to prevent filtrate from leaking therebetween may be used and the invention is not limited to any particular means.

Figure 3:
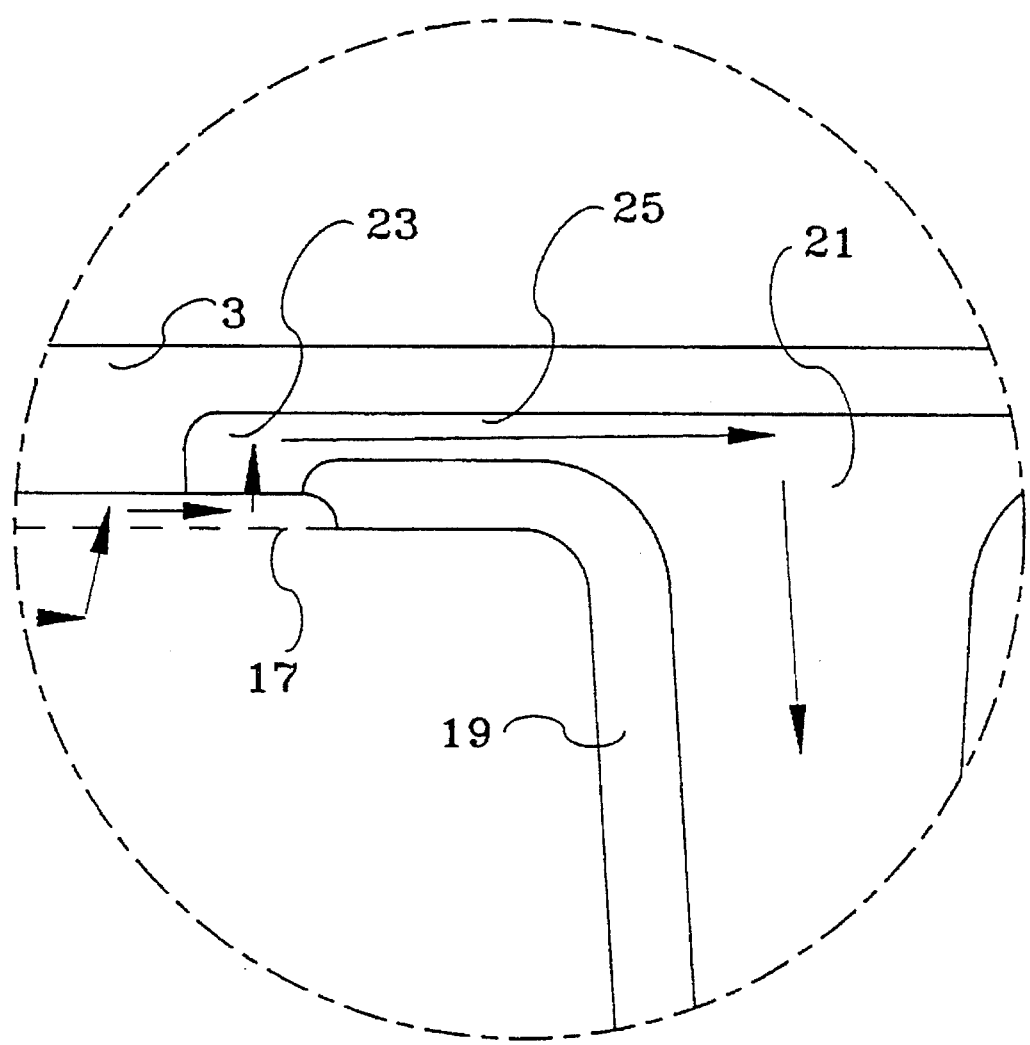
FIG. 3 depicts an enlarged sectional view of the filter element depicted in FIG. 2 useable within the filtration apparatus and constructed in accordance with the principles of the present invention.

Once the filter unit 3 is inserted into the housing 1 in the manner depicted in FIG. 1 the filtrate collector such as the filtrate collecting cup 5 should be attached to the housing. Liquid such as a macro-molecular solution to be filtered and concentrated is placed within the housing 1 and the filtration apparatus placed within a centrifuge, or within a vacuum filtering means for filtration, filtrate will flow through the filter unit as depicted in FIG. 3. Filtrate passes through the membrane 17 and into the inlet 23 and through a passage 25 and filtrate port 21 through the neck 19. Once passing through the neck 19, the filtrate is preferably collected within the filtrate collecting cup 5 (FIG. 1), or other suitable filtrate collecting means.

Referring to FIG. 4, during filtration the forces exerted on the liquid solution being filtered result in liquid flowing through the area between the housing 1 and filter unit 3, which is preferably ring-shaped in order to maximize the filter membrane area for filtration. The force exerted upon the liquid solution forces filtrate through the semi-permeable membrane, as shown in FIG. 3. Filtration will automatically stop when the level of concentrate remaining within the housing 1 reaches the same level as the filter membrane within the housing as is shown in FIG. 4. Accordingly, the filtration apparatus may be constructed to not filter to dryness. During filtration, filtrate will flow through the neck 19 into the filtrate collecting cup 5 (not shown in FIG. 4) until the level of concentrate within the housing 1 reaches the level of the semi-permeable membrane. At this time, filtration will cease and the filtrate collecting cup 5 may be removed. The concentrate collecting cup 7 (not shown in FIG. 4) may then be threadably engaged to the collar 15. The concentrate collecting cup 7 contains a protrusion 39 (FIG. 1) which contacts the neck 19 of the filter element when the concentrate collecting cup is threadably engaged to the collar 15 displacing the filter unit 3 and releasing the seal between the nipple 13 and filter unit 3. Concentrate is then allowed to flow through the nipple 13 and into the concentrate collecting cup 7.

The filtration device constructed in accordance with the principles of the present invention allows dense molecules which may cause fouling to be forced away from the membrane surface 17 by centrifugal force while simultaneously allowing filtrate to flow into a filtrate collection means. This is accomplished by orienting the membrane surface 17 of the filtration device in a direction opposite to the centrifugal force.

Figure 5:
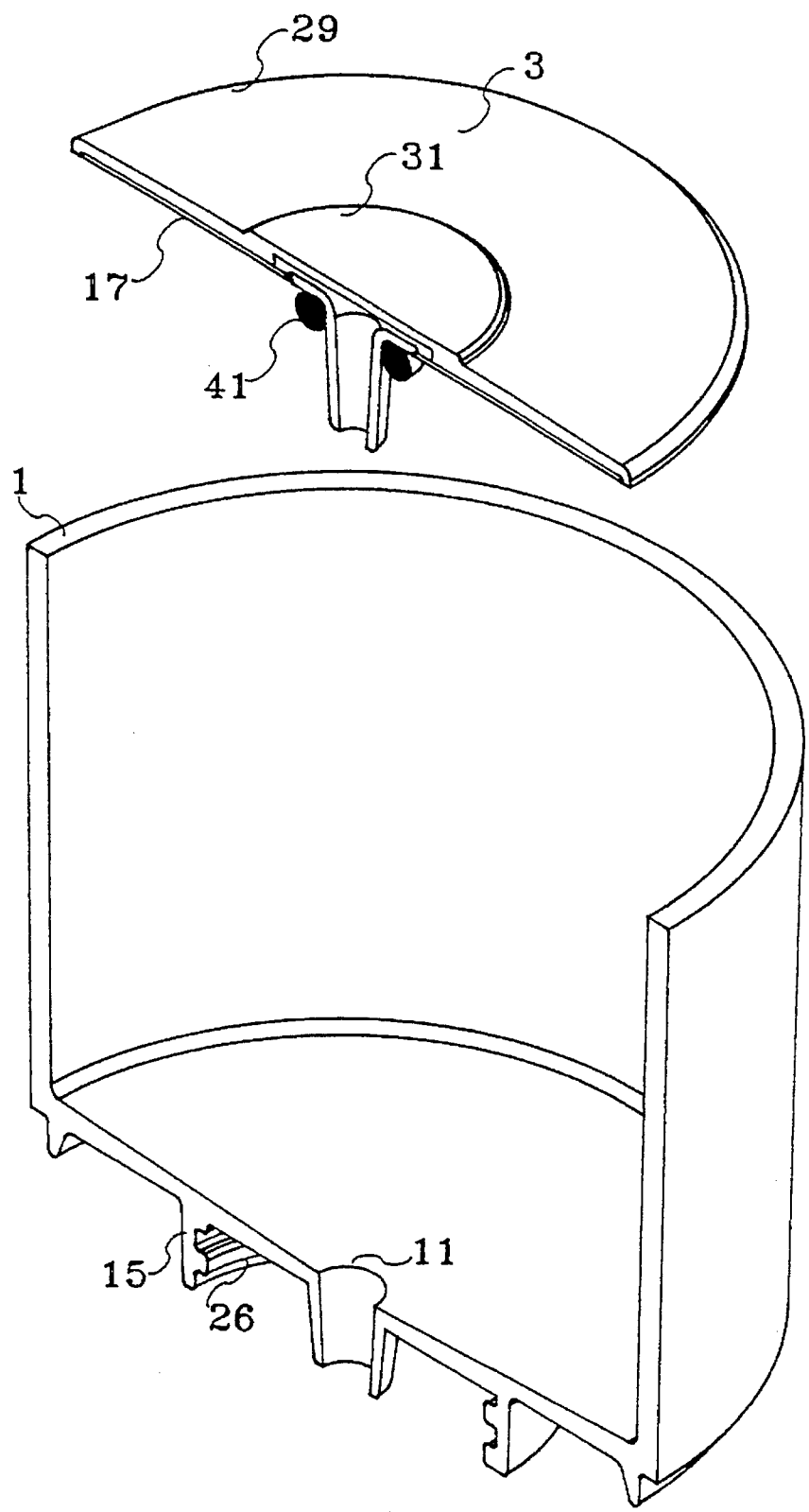
FIG. 5 depicts an alternative embodiment of the filtration apparatus constructed in accordance with the principles of the present invention having a gasket or O-ring as a sealing means between the housing and filter unit thereof.
Figure 6:
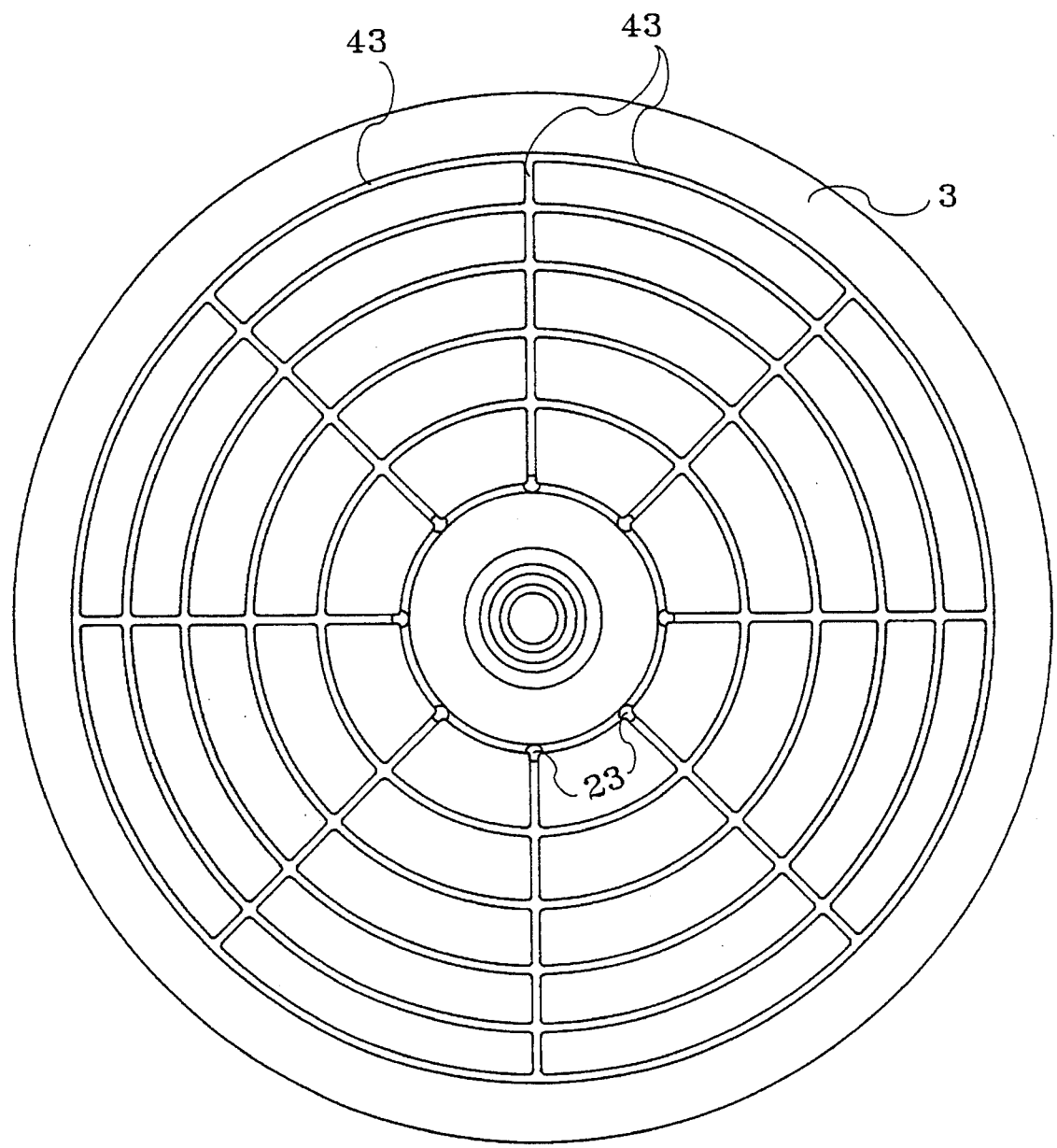
FIG. 6 depicts a bottom view of the first side of the filter unit depicted in FIG. 2 having the membrane removed therefrom constructed in accordance with the principles of the present invention.

FIG. 5 depicts an alternative means for sealing the area between the filter unit 3 and the housing 1 to prevent concentrate from flowing therebetween and mixing with filtrate. In this embodiment, an O-ring or gasket 41 is placed around the discharge opening 21 at the base of the first side of the filter element 3. Also, an O-ring may be placed around the nipple 13 and sized to fit within the discharge opening to create a seal 11. To facilitate the flow of filtrate through the membrane and into the one or more inlets 23 a plurality of channels 43 may be located on the first side of the filter element 3 as depicted in FIG. 6. Preferably, the channels intersect with one another thereby leading to the one or more inlets 23 so that filtrate may collect with in the channels and flow into the one or more inlets 23 through the filtrate opening 21 and through the neck 19.

The features in the filtration apparatus disclosed in U.S. Pat. No. 5,112,484 issued on May 12, 1992 and incorporated into the specification herein by reference, may be used in the filtration apparatus in accordance with the principles of the present invention. Specifically, the variable dead stop features, sealing techniques, techniques for affixing the filtration collecting means, and techniques for sealing the concentrate collecting means, and for venting the housing and filtrate collecting cups may be used in accordance with the principles of the present invention. Moreover, the means for retrieving the concentrate from the housing using the specifically configured concentrate collecting cup disclosed in U.S. Pat. No. 5,112,484 may also be used. In addition, the techniques for using a vacuum suction device disclosed in U.S. Pat. No. 5,112,484 and incorporated herein by reference may also be used in accordance with the principles of the present invention.

Although the invention has been disclosed in connection with the embodiments depicted herein, it will be apparent to one of ordinary skill in the art that various modifications and substitutions may be made to these embodiments without departing in any way from the scope of the invention as defined in the following claims.

What is claimed is:

1. A filtration apparatus for separating filtrate and concentrate from a solution comprising;

a housing having a discharge opening therein and being capable of containing a liquid solution therein;

a filter unit insertable within the housing having a first side and an opposing second side, wherein the first side of the filter unit faces in the same direction as the discharge opening of the housing, the filter unit comprising, a semipermeable membrane located on the first side and capable of separating filtrate and retentate, a gap between the filter unit and the housing wall to allow passage of the solution to be filtered, at least one filtrate inlet to said discharge opening located on the first side, wherein the semipermeable membrane covers the at least one inlet, a filtrate port located on the first side and being in fluid flow relationship with the at least one inlet, wherein the filtrate port is oriented to allow filtrate flowing therethrough to flow into the discharge opening of the housing; and means for sealing the filter unit to the housing for preventing concentrate within the housing from flowing within the discharge opening.

2. The apparatus of claim 2 wherein said filter unit comprises a neck protruding from the first side thereof, the neck having the filtrate port therein and being insertable into the discharge opening of the housing.

3. The apparatus of claim 2 wherein the sealing means comprises an interface between the neck of the filter unit and the discharge opening of the housing.

4. The apparatus of claim 3 further comprising means for securing a filtrate collecting cup to the housing.

5. The apparatus of claim 1 further comprising a concentrate collector.

6. The apparatus of claim 5, wherein the concentrate collector comprises a concentrate collecting cup having a protruding member therein insertable within the discharge opening of the housing, and adapted to displace the filter unit when the protruding member is inserted into the discharge opening to allow concentrate from within the housing to flow through the discharge opening and into the concentrate cup.

7. The apparatus of claim 6 further comprising means for receiving the concentrate cup.

8. The apparatus of claim 7 wherein said means for receiving said concentrate cup comprises a threaded member capable of receiving a threaded portion of the concentrate cup.

9. The apparatus of claim 1 further comprising a filtrate collector.

10. The apparatus of claim 9 wherein the filtrate collector comprises a filtrate collecting cup.

11. The apparatus of claim 1 wherein the housing comprises a removable cap.

12. The apparatus of claim 11 wherein the at least one filter inlet comprises a plurality of filter inlets located around the periphery of a portion of the first side of the filter unit having the neck protruding therefrom.

13. The apparatus of claim 11 wherein the semipermeable membrane is sealed to the first side of the filter unit.

14. The apparatus of claim 1 wherein the first side of the filter unit comprises at least one channel thereon for allowing filtrate to flow therein to the at least one inlet.

15. A filter unit for a filtration apparatus including a housing having a discharge opening therein, the filter unit comprising:

a first side opposing to a second side, said first side having a semipermeable membrane located thereon capable of separating filtrate and concentrate, wherein said semipermeable membrane and said first side are disposed to face the same direction as the discharge opening;

a gap between the filter unit and the housing wall, to allow passage of the solution to be filtered, at least one filtrate inlet to said discharge opening located on the first side, wherein said semipermeable membrane covers the at least one inlet;

a filtrate port located on the first side and being in fluid flow relationship with the at least one inlet, wherein the filtrate port is oriented to allow filtrate flowing therethrough to flow into the discharge opening of the filtration apparatus.

16. The filter unit of claim 15 wherein the filter unit comprises a neck protruding from the first side thereof, the neck having the filtrate port therein and being insertable into the discharge opening of the housing.

17. The filter unit of claim 16 wherein the sealing means comprises an interface between the neck of the filter unit and the discharge opening of the housing.

18. The filter unit of claim 16 wherein the first side of the filter unit comprises at least one channel thereon for allowing filtrate to flow therein to the at least one inlet.

19. The filter unit of claim 18 wherein the at least one filter inlet comprises a plurality of filter inlets located around the periphery of a portion of the first side of the filter unit having the neck protruding therefrom.

20. The apparatus of claim 19 wherein the semipermeable membrane is sealed to said first side of said filter unit.

\* \* \* \* \*